US008432541B2

(12) United States Patent
Rich

(10) Patent No.: US 8,432,541 B2
(45) Date of Patent: Apr. 30, 2013

(54) OPTICAL SYSTEM FOR A FLOW CYTOMETER WITH AN INTERROGATION ZONE

(75) Inventor: Collin A. Rich, Ypsilanti, MI (US)

(73) Assignee: Accuri Cytometers, Inc., Ann Arbor, MI (US)

( * ) Notice: Subject to any disclaimer, the term of this patent is extended or adjusted under 35 U.S.C. 154(b) by 293 days.

(21) Appl. No.: 12/939,836

(22) Filed: Nov. 4, 2010

(65) Prior Publication Data

US 2011/0058163 A1 Mar. 10, 2011

Related U.S. Application Data

(63) Continuation-in-part of application No. 12/337,517, filed on Dec. 17, 2008, now Pat. No. 7,843,561.

(60) Provisional application No. 61/014,376, filed on Dec. 17, 2007.

(51) Int. Cl.
*G01N 1/10* (2006.01)
(52) U.S. Cl.
USPC ............................................. 356/246; 356/73
(58) Field of Classification Search .............. 356/244, 356/246, 73, 432–440, 335–343, 39
See application file for complete search history.

(56) References Cited

U.S. PATENT DOCUMENTS

| 3,347,273 A | 10/1967 | Russell |
|---|---|---|
| 3,601,128 A | 8/1971 | Hakim |
| 3,672,402 A | 6/1972 | Bloemer |
| 3,819,272 A * | 6/1974 | Crozier et al. ............. 356/138 |
| 4,112,735 A | 9/1978 | Mcknight |
| 4,138,879 A | 2/1979 | Liebermann |
| 4,371,786 A | 2/1983 | Kramer |
| 4,448,538 A | 5/1984 | Mantel |
| 4,559,454 A | 12/1985 | Kramer |
| 4,570,639 A | 2/1986 | Miodownik |
| 4,691,829 A | 9/1987 | Auer |
| 4,755,021 A | 7/1988 | Dyott |
| 4,790,653 A | 12/1988 | North, Jr. |
| 4,818,103 A | 4/1989 | Thomas et al. |
| 4,824,641 A | 4/1989 | Williams |
| 4,826,660 A | 5/1989 | Smith et al. |
| 4,844,610 A | 7/1989 | North, Jr. |
| 4,933,813 A | 6/1990 | Berger |
| 5,028,127 A | 7/1991 | Spitzberg |
| 5,040,890 A | 8/1991 | North, Jr. |
| 5,043,706 A | 8/1991 | Oliver |
| 5,083,862 A | 1/1992 | Rusnak |

(Continued)

FOREIGN PATENT DOCUMENTS

| EP | 466490 A | 1/1992 |
|---|---|---|
| EP | 1391611 A | 2/2004 |

(Continued)

*Primary Examiner* — Hoa Pham
(74) *Attorney, Agent, or Firm* — Jeffrey Schox

(57) ABSTRACT

The optical system of the preferred embodiments includes a first light source that creates a first beam of a first wavelength, a first collimating element that collimates the first beam, a second light source 102 that creates a second beam of a second wavelength, a second collimating element that collimates the second beam, a beam combining element that combines the collimated beams, and a focusing element that focuses the combined collimated beam to a single point.

18 Claims, 3 Drawing Sheets

U.S. PATENT DOCUMENTS

| | | |
|---|---|---|
| 5,138,868 A | 8/1992 | Long |
| 5,139,609 A | 8/1992 | Fields et al. |
| 5,150,037 A | 9/1992 | Kouzuki |
| 5,150,313 A | 9/1992 | Van Den Engh et al. |
| 5,155,543 A | 10/1992 | Hirako |
| 5,204,884 A | 4/1993 | Leary et al. |
| 5,224,058 A | 6/1993 | Mickaels et al. |
| 5,230,026 A | 7/1993 | Ohta et al. |
| 5,270,548 A | 12/1993 | Steinkamp |
| 5,301,685 A | 4/1994 | Guirguis |
| 5,308,990 A | 5/1994 | Takahashi et al. |
| 5,367,474 A | 11/1994 | Auer et al. |
| 5,374,395 A | 12/1994 | Robinson et al. |
| 5,395,588 A | 3/1995 | North, Jr. et al. |
| 5,403,552 A | 4/1995 | Pardikes |
| 5,466,946 A | 11/1995 | Kleinschmitt et al. |
| 5,469,375 A | 11/1995 | Kosaka |
| 5,539,386 A | 7/1996 | Elliott |
| 5,552,885 A | 9/1996 | Steen |
| 5,559,339 A | 9/1996 | Domanik et al. |
| 5,616,124 A | 4/1997 | Hague et al. |
| 5,684,480 A | 11/1997 | Jansson |
| 5,739,902 A | 4/1998 | Gjelsnes et al. |
| 5,797,430 A | 8/1998 | Becke et al. |
| 5,798,222 A | 8/1998 | Goix |
| 5,804,507 A | 9/1998 | Perlov et al. |
| 5,883,378 A | 3/1999 | Irish et al. |
| 5,920,388 A | 7/1999 | Sandberg et al. |
| 5,960,129 A | 9/1999 | Kleinschmitt |
| 5,981,180 A | 11/1999 | Chandler et al. |
| 6,016,376 A | 1/2000 | Ghaemi et al. |
| 6,039,078 A | 3/2000 | Tamari |
| 6,067,157 A | 5/2000 | Altendorf |
| 6,070,477 A | 6/2000 | Mark |
| 6,091,502 A | 7/2000 | Weigl et al. |
| 6,097,485 A | 8/2000 | Lievan |
| 6,108,463 A | 8/2000 | Herron et al. |
| 6,110,427 A | 8/2000 | Uffenheimer |
| 6,115,065 A | 9/2000 | Yadid-Pecht et al. |
| 6,139,800 A | 10/2000 | Chandler |
| 6,154,276 A | 11/2000 | Mariella, Jr. |
| 6,156,208 A | 12/2000 | Desjardins et al. |
| 6,181,319 B1 | 1/2001 | Fujita et al. |
| 6,183,697 B1 | 2/2001 | Tanaka et al. |
| 6,288,783 B1 | 9/2001 | Auad |
| 6,377,721 B1 | 4/2002 | Walt et al. |
| 6,382,228 B1 | 5/2002 | Cabuz et al. |
| 6,403,378 B1 | 6/2002 | Phi-Wilson et al. |
| 6,427,521 B2 | 8/2002 | Jakkula et al. |
| 6,431,950 B1 | 8/2002 | Mayes |
| 6,456,769 B1 | 9/2002 | Furusawa et al. |
| 6,469,787 B1 | 10/2002 | Meyer et al. |
| 6,473,171 B1 | 10/2002 | Buttry et al. |
| 6,519,355 B2 | 2/2003 | Nelson |
| 6,522,775 B2 | 2/2003 | Nelson |
| 6,568,271 B2 | 5/2003 | Shah et al. |
| 6,587,203 B2 | 7/2003 | Colon |
| 6,602,469 B1 | 8/2003 | Maus et al. |
| 6,636,623 B2 | 10/2003 | Nelson et al. |
| 6,675,835 B2 | 1/2004 | Gerner et al. |
| 6,694,799 B2 | 2/2004 | Small |
| 6,700,130 B2 | 3/2004 | Fritz |
| 6,710,871 B1 | 3/2004 | Goix |
| 6,718,415 B1 | 4/2004 | Chu |
| 6,778,910 B1 | 8/2004 | Vidal et al. |
| 6,809,804 B1 | 10/2004 | Yount et al. |
| 6,816,257 B2 | 11/2004 | Goix |
| 6,825,926 B2 | 11/2004 | Turner et al. |
| 6,852,284 B1 | 2/2005 | Holl et al. |
| 6,859,570 B2 | 2/2005 | Walt et al. |
| 6,869,569 B2 | 3/2005 | Kramer |
| 6,872,180 B2 | 3/2005 | Reinhardt et al. |
| 6,890,487 B1 | 5/2005 | Sklar et al. |
| 6,897,954 B2 | 5/2005 | Bishop et al. |
| 6,901,964 B2 | 6/2005 | Kippe et al. |
| 6,908,226 B2 | 6/2005 | Siddiqui et al. |
| 6,912,904 B2 | 7/2005 | Storm, Jr. et al. |
| 6,936,828 B2 | 8/2005 | Saccomanno |
| 6,941,005 B2 | 9/2005 | Lary et al. |
| 6,944,322 B2 | 9/2005 | Johnson et al. |
| 7,009,189 B2 | 3/2006 | Saccomanno |
| 7,012,689 B2 | 3/2006 | Sharpe |
| 7,019,834 B2 | 3/2006 | Sebok et al. |
| 7,024,316 B1 | 4/2006 | Ellison et al. |
| 7,061,595 B2 | 6/2006 | Cabuz et al. |
| 7,075,647 B2 | 7/2006 | Christodoulou |
| 7,105,355 B2 | 9/2006 | Kurabayashi et al. |
| 7,106,442 B2 | 9/2006 | Silcott et al. |
| 7,113,266 B1 | 9/2006 | Wells |
| 7,130,046 B2 | 10/2006 | Fritz et al. |
| 7,232,687 B2 | 6/2007 | Lary et al. |
| 7,262,838 B2 | 8/2007 | Fritz |
| 7,274,316 B2 | 9/2007 | Moore |
| 7,328,722 B2 | 2/2008 | Rich et al. |
| 7,362,432 B2 | 4/2008 | Roth |
| 7,403,125 B2 | 7/2008 | Rich |
| 7,471,393 B2 | 12/2008 | Trainer |
| 7,520,300 B2 | 4/2009 | Rich et al. |
| 7,628,956 B2 | 12/2009 | Jindo |
| 7,738,099 B2 | 6/2010 | Morrell |
| 7,739,060 B2 | 6/2010 | Goebel et al. |
| 7,776,268 B2 | 8/2010 | Rich |
| 7,780,916 B2 | 8/2010 | Bair et al. |
| 7,843,561 B2 | 11/2010 | Rich |
| 7,857,005 B2 | 12/2010 | Rich et al. |
| 7,903,706 B2 * | 3/2011 | O'Shaughnessy et al. ..... 372/34 |
| 7,981,661 B2 | 7/2011 | Rich |
| 7,996,188 B2 | 8/2011 | Olson et al. |
| 8,017,402 B2 | 9/2011 | Rich |
| 8,031,340 B2 | 10/2011 | Rich et al. |
| 2001/0014477 A1 | 8/2001 | Pelc et al. |
| 2001/0039053 A1 | 11/2001 | Liseo et al. |
| 2002/0028434 A1 | 3/2002 | Goix et al. |
| 2002/0049782 A1 | 4/2002 | Herzenberg et al. |
| 2002/0059959 A1 | 5/2002 | Qatu et al. |
| 2002/0080341 A1 | 6/2002 | Kosaka |
| 2002/0123154 A1 | 9/2002 | Burshteyn et al. |
| 2002/0192113 A1 | 12/2002 | Uffenheimer et al. |
| 2003/0035168 A1 | 2/2003 | Qian et al. |
| 2003/0048539 A1 | 3/2003 | Oostman et al. |
| 2003/0054558 A1 | 3/2003 | Kurabayashi et al. |
| 2003/0062314 A1 | 4/2003 | Davidson et al. |
| 2003/0072549 A1 | 4/2003 | Facer et al. |
| 2003/0078703 A1 | 4/2003 | Potts et al. |
| 2003/0129090 A1 | 7/2003 | Farrell |
| 2003/0134330 A1 | 7/2003 | Ravkin et al. |
| 2003/0148379 A1 | 8/2003 | Roitman et al. |
| 2003/0175157 A1 | 9/2003 | Micklash et al. |
| 2003/0202175 A1 | 10/2003 | Van Den Engh et al. |
| 2003/0211009 A1 | 11/2003 | Buchanan |
| 2003/0223061 A1 | 12/2003 | Sebok et al. |
| 2003/0235919 A1 | 12/2003 | Chandler |
| 2004/0031521 A1 | 2/2004 | Vrane et al. |
| 2004/0048362 A1 | 3/2004 | Trulson et al. |
| 2004/0112808 A1 | 6/2004 | Takagi et al. |
| 2004/0119974 A1 | 6/2004 | Bishop et al. |
| 2004/0123645 A1 | 7/2004 | Storm et al. |
| 2004/0131322 A1 | 7/2004 | Ye et al. |
| 2004/0143423 A1 | 7/2004 | Parks et al. |
| 2004/0175837 A1 | 9/2004 | Bonne et al. |
| 2004/0197768 A1 | 10/2004 | Glencross |
| 2004/0201845 A1 | 10/2004 | Quist et al. |
| 2004/0246476 A1 | 12/2004 | Bevis et al. |
| 2005/0044110 A1 | 2/2005 | Herzenberg et al. |
| 2005/0047292 A1 | 3/2005 | Park et al. |
| 2005/0057749 A1 | 3/2005 | Dietz et al. |
| 2005/0069454 A1 | 3/2005 | Bell |
| 2005/0073686 A1 | 4/2005 | Roth et al. |
| 2005/0078299 A1 | 4/2005 | Fritz et al. |
| 2005/0105091 A1 | 5/2005 | Lieberman et al. |
| 2005/0162648 A1 | 7/2005 | Auer et al. |
| 2005/0163663 A1 | 7/2005 | Martino et al. |
| 2005/0195605 A1 | 9/2005 | Saccomanno et al. |
| 2005/0195684 A1 | 9/2005 | Mayer |
| 2005/0252574 A1 | 11/2005 | Khan et al. |
| 2006/0002634 A1 | 1/2006 | Riley et al. |
| 2006/0015291 A1 | 1/2006 | Parks et al. |

| | | |
|---|---|---|
| 2006/0023219 A1 | 2/2006 | Meyer et al. |
| 2006/0161057 A1 | 7/2006 | Weber et al. |
| 2006/0177937 A1 | 8/2006 | Kurabayashi et al. |
| 2006/0219873 A1 | 10/2006 | Martin et al. |
| 2006/0280061 A1* | 12/2006 | Koreeda et al. ............ 369/44.23 |
| 2006/0281143 A1 | 12/2006 | Liu et al. |
| 2006/0286549 A1 | 12/2006 | Sohn et al. |
| 2007/0003434 A1 | 1/2007 | Padmanabhan et al. |
| 2007/0041013 A1 | 2/2007 | Fritz et al. |
| 2007/0096039 A1 | 5/2007 | Kapoor et al. |
| 2007/0124089 A1 | 5/2007 | Jochum et al. |
| 2007/0127863 A1 | 6/2007 | Bair et al. |
| 2007/0144277 A1 | 6/2007 | Padmanabhan et al. |
| 2007/0212262 A1 | 9/2007 | Rich |
| 2007/0224684 A1 | 9/2007 | Olson et al. |
| 2007/0243106 A1 | 10/2007 | Rich |
| 2008/0055595 A1 | 3/2008 | Olson et al. |
| 2008/0064113 A1 | 3/2008 | Goix et al. |
| 2008/0092961 A1 | 4/2008 | Bair et al. |
| 2008/0152542 A1 | 6/2008 | Ball et al. |
| 2008/0215297 A1 | 9/2008 | Goebel et al. |
| 2008/0228444 A1 | 9/2008 | Olson et al. |
| 2008/0246949 A1* | 10/2008 | Harris et al. ................... 356/51 |
| 2009/0104075 A1 | 4/2009 | Rich |
| 2009/0174881 A1 | 7/2009 | Rich |
| 2009/0201501 A1 | 8/2009 | Bair et al. |
| 2009/0202130 A1 | 8/2009 | George et al. |
| 2009/0216478 A1 | 8/2009 | Estevez-Labori |
| 2009/0257339 A1* | 10/2009 | Katayama ............... 369/112.23 |
| 2009/0260701 A1 | 10/2009 | Rich et al. |
| 2009/0293910 A1 | 12/2009 | Ball et al. |
| 2010/0008204 A1* | 1/2010 | Bae et al. ...................... 369/103 |
| 2010/0012853 A1 | 1/2010 | Parks et al. |
| 2010/0032584 A1 | 2/2010 | Dayong et al. |
| 2010/0118298 A1 | 5/2010 | Bair et al. |
| 2010/0119298 A1 | 5/2010 | Huang |
| 2010/0302536 A1 | 12/2010 | Ball et al. |
| 2010/0319469 A1 | 12/2010 | Rich |
| 2010/0319786 A1 | 12/2010 | Bair et al. |
| 2011/0008816 A1 | 1/2011 | Ball et al. |
| 2011/0061471 A1 | 3/2011 | Rich et al. |
| 2011/0306031 A1 | 12/2011 | Rich |

FOREIGN PATENT DOCUMENTS

| | | |
|---|---|---|
| EP | 1396736 A2 | 3/2004 |
| EP | 1521076 A | 4/2005 |
| JP | 356169978 | 12/1981 |
| JP | Sho5913689 | 3/1984 |
| JP | Sho6353901 | 4/1988 |
| JP | 04086546 H | 3/1992 |
| JP | 6194299 A | 7/1994 |
| JP | 06221988 H | 12/1994 |
| JP | 7260084 A | 10/1995 |
| JP | 08201267 H | 8/1996 |
| JP | 09288053 H | 11/1997 |
| JP | 10227737 A | 8/1998 |
| JP | 2001050887 A | 2/2001 |
| JP | 2001170062 A | 6/2001 |
| JP | 2003262201 A | 9/2003 |
| JP | 200477484 | 3/2004 |
| WO | 9956052 | 11/1999 |
| WO | 0194914 | 12/2001 |
| WO | 2005017499 A | 2/2005 |
| WO | 2005068971 A | 7/2005 |
| WO | 2005073694 A | 8/2005 |
| WO | 2005091893 A | 10/2005 |
| WO | 2006055722 A | 5/2006 |
| WO | 2007067577 A | 6/2007 |
| WO | 2007100723 A | 9/2007 |
| WO | 2007103969 A | 9/2007 |
| WO | 2007136749 A | 11/2007 |
| WO | 2008058217 A | 5/2008 |
| WO | 2010101623 A | 9/2010 |

* cited by examiner

OPTICAL SYSTEM FOR A FLOW CYTOMETER WITH AN INTERROGATION ZONE

CROSS-REFERENCE TO RELATED APPLICATIONS

This application is a continuation-in-part of prior application Ser. No. 12/337,517 filed 17 Dec. 2008, which claims the benefit of U.S. Provisional Application No. 61/014,376 filed 17 Dec. 2007, which are both incorporated in their entirety by this reference.

TECHNICAL FIELD

This invention relates generally to the flow cytometer field, and more specifically to a new and useful optical system in the flow cytometry field.

BACKGROUND

The conventional optical system for flow cytometers requires aligning the light sources in relation to the lenses to shine multiple frequencies of light on a sample simultaneously. Since the light source affects the detection of each of the detector subsystems, this alignment must be precise or the performance of the system is dramatically reduced. To achieve this precision, however, requires expensive manufacturing techniques and/or time-consuming manual alignment. Thus, there is a need in the flow cytometer field to create a new and useful optical system. This invention provides such new and useful optical system.

DESCRIPTION OF THE PREFERRED EMBODIMENTS

The following description of the preferred embodiments of the invention is not intended to limit the invention to these preferred embodiments, but rather to enable any person skilled in the art to make and use this invention.

Figure 1:
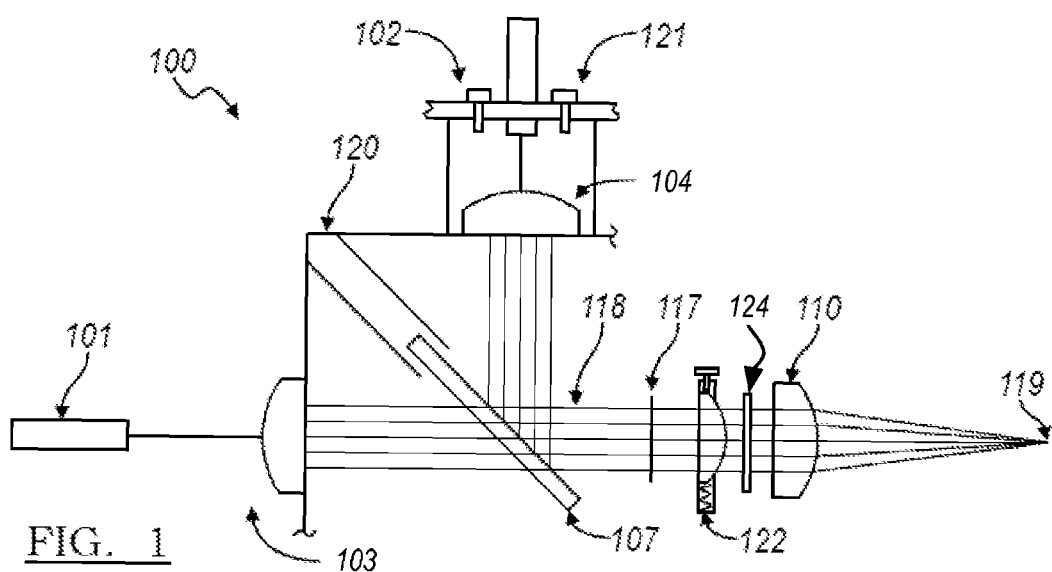
FIG. 1 is a schematic representation of a first preferred embodiment of the invention.

As shown in FIG. 1, the optical system of the preferred embodiments includes a first light source 101 that creates a first beam of a first wavelength, a first collimating element 103 that collimates the first beam, a second light source 102 that creates a second beam of a second wavelength, which is different than the first wavelength, a second collimating element 104 that collimates the second beam, a beam combining element 107 that combines the collimated beams of the first and second collimating elements to form a combined collimated beam that is multichromatic, and a focusing element no that focuses the combined collimated beam to a single point. The optical system 100 was specifically designed to focus a multichromatic beam at a single point in an interrogation zone of a flow cytometer, but may alternatively be used in any suitable device or system. The optical system 100 overcomes the disadvantages of the conventional optical systems for flow cytometers because, even if the light sources are not perfectly aligned with each other (or the beam combing element 107), enough light from the light sources will be combined to form an adequate multichromatic beam.

Figure 4:
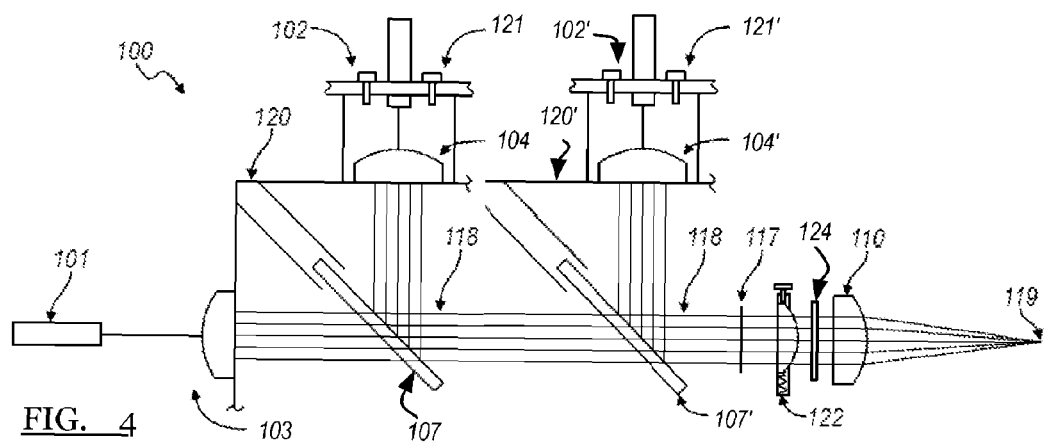
FIG. 4 is a schematic representation of an alternative embodiment of the invention.

The light sources 101 and 102, which are preferably mounted to the base, function as two independent light sources. The light sources 101 and 102 are preferably lasers of different light frequencies. The first light source 101 is preferably a blue laser and the second light source 102 is preferably a red laser, but the light sources 101 and 102 may alternatively be any two different light sources that vary in wavelength, frequency, phase, polarization, light signal, and/or any suitable light characteristic. The light sources 101 and 102 may additionally be generated from a laser diode and/or any suitable optical setup to generate a suitable light source. In an alternative embodiment, as shown in FIG. 4, the system 100 may further include a third light source (not shown) that produces a third beam with yet another light characteristic.

The collimating elements 103 and 104 function to collimate light from the light sources 101 and 102, respectively. The collimated elements 103 and 104 preferably convert light into a collimated beam where light energy is uniformly (or near uniformly) distributed across a larger area. The collimated beam may alternatively have a gradient of light energy, a Gaussian distribution, or any suitable beam parameter of distributed light energy. The collimated beam preferably travels in a single direction and does not disperse radially outward from a point. The collimating element 103, which is preferably mounted to the first light source 101, is located between the first light source 101 and the beam combining element 107. The collimating element 104, which is preferably mounted to the second light source 102, is located between the second light sources 102 and the beam combining element 107. In one version, one or both of the collimating elements 103 and 104 may be combined or integrated with the light sources 101 and 102, such that each light source 101 and 102 produces collimated light. In another version, one or both of the collimating elements 103 and 104 may be fastened to, or otherwise optically communicating with, the light sources 101 and 102. The collimating elements 103 and 104 are preferably conventional collimating lens, but may alternatively be any suitable device to collimate the beams from the light sources 101 and 102.

The beam combining element 107, which is preferably mounted to the base, functions to combine the collimated beams from the light sources 101 and 102. The light between the beam combining element 107 and the focusing element 110 is preferably a collimated beam. Additionally, the light entering the beam combining element 107 is preferably a collimated beam (or beams). The collimated beam functions to reduce the tolerances and/or difficulty of optical alignment and manufacturing tolerances of the optical system. The loss of light due to minor misalignment (where at least a designated minimum percentage of light hits a target) is preferably allowable due to the light being a collimated beam. A collimated beam is preferably used to traverse the longer distances of the optical system. In a first version, the beam combining element 107 is a conventional beam splitter. The beam splitter is preferably selectively transmissive and preferably allows the light of an appropriate bandwidth from at least one light source to pass through it, and the beam splitter is also preferably reflective to allow at least one other light source to be reflected from it. Preferably, the collimated light from at least one light source 102 passes through the beam splitter 107, while collimated light from at least one other light source 101 is reflected off the other side of the beam splitter 107, to create multichromatic collimated beams 118. In other versions, the beam combining element 107 may include beam combiners, mirrors, optical prisms, fiber optics, and/or any suitable device or method to combine the beams from the light sources 101 and 102.

Figure 2:
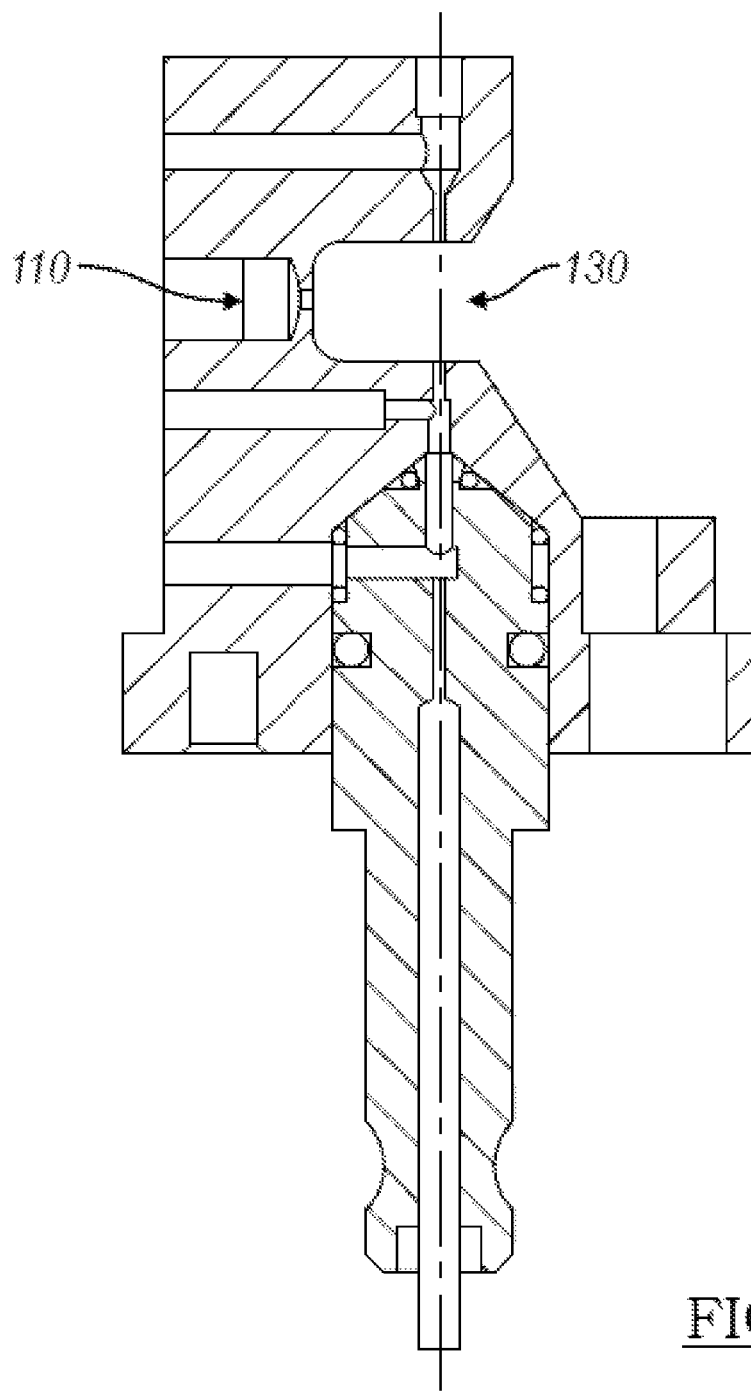
FIG. 2 is a cross-sectional view of a flow cell of the preferred embodiment of the invention.
Figure 3:
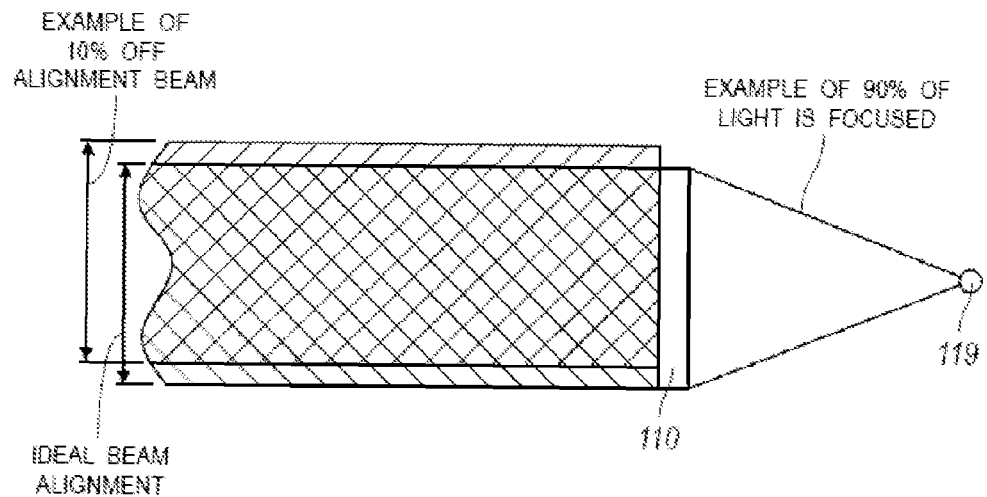
FIG. 3 is a detailed schematic representation of a collimated beam that is incident on a focusing element of the preferred embodiment of the invention.

The focusing element 110 functions to focus the multichromatic collimated beams 118 to a single point. The focusing element 110 is preferably an achromatic lens, but may also be multiple lenses and/or lens configurations or any other suitable focusing element. The focusing element 110 is preferably positioned such that the light is focused on the interrogation zone 119 of the flow cytometer. As shown in FIG. 3, the focusing element preferably allows for slight misalignment of the multichromatic collimated beam. The focusing element may additionally allow for slight misalignment of the first light source 101 with respect to the collimated light from the second light source 102. The focusing element preferably has a target area on the focusing element where incident light is focused on the interrogation zone 119. The target area is preferably suitably large (e.g. magnitude of a collimated beam width) to allow for variation and small errors in optical alignment. The light energy of the multichromatic collimated beam is preferably distributed over the area of the collimated beam cross-section such that a majority or sufficient amount of light energy is incident on the target area. For example, a multichromatic collimated beam may be misaligned by 10% but the focusing element 110 is preferably able to focus 90% of the light (the part that is incident on the target area) on the interrogation zone and this is preferably sufficient. The target area is preferably uniform in focusing capability but may alternatively have a distribution of focusing capability, or any suitable mapping of focusing capability and may be any suitable shape or size. In a first version, as shown in FIG. 2, the focusing element 110 is preferably mounted to a flow cell 130 of a flow cytometer. The flow cell 130 is preferably similar to the one disclosed in PCT Application number US2007/083991 filed 7 Nov. 2007, which is incorporated in its entirety by this reference, but may alternatively be any suitable interrogation zone 119 of a flow cytometer. The light within the flow cell 130 (the light from the focusing element 110) is preferably an uncollimated (or focused) beam. The flow cell 130 is preferably manufactured and/or controlled with tight dimensional and optical tolerances such that precise optical alignment is achieved within the flow cell 130. Additionally, the distance the laser light travels is preferably minimized to reduce the likelihood of misalignment. In a second version, the focusing element 110 may be mounted, either directly or indirectly, to the beam combining element 107, a bracket 120, and/or to a base.

In an alternative embodiment, as shown in FIG. 4, the optical system 100 includes one or more additional light sources 102', collimating elements 104', and/or beam combining elements 107'. Groups of at least one light source, at least one collimating element, and at least one beam combining element may form optical "stages" in which additional light beams are added to the combined collimated beam, preferably similar to the group of the second light source 102, the second collimating element 104, and the beam combining element 107 but alternatively in any suitable manner. The optical system 100 may include second, third, fourth, or any suitable number of optical stages to add collimated light beams of additional wavelengths or other characteristics to the combined collimated beam 118, preferably before the focusing element 110 focuses the combined collimated beams 118.

In one variation, the optical system 100 includes a removable filter 117 that functions to filter the multichromatic collimated beams 118 from the beamsplitter 107. The filter 117 is preferably removable, replaceable, tunable, or variable in some fashion by the user of the system and/or by a central processor. Alternatively, the filter may also be a coating on a beamsplitter 107, and/or a coating on the focusing element 110. The removable filter 117 may alternatively filter light from the first light source 101 and/or second light source 102. Additionally, a plurality of filters may alternatively be used to filter light during multiple suitable stage of the optical system. The filter 117 functions to absorb spurious emissions and/or to "clean up" the light. The optical system 100 may, however, omit the removable filter or may include a filter and/or filters that are not variable.

In another variation, the optical system 100 includes a bracket 120 that functions to align and hold the light sources 101 and 102, the collimating elements 103 and 104, and the beam splitter 107 in the correct positions to produce collimated multichromatic light. The bracket 120 is preferably mounted to a base or surface of a flow cytometer. The bracket 120 preferably achieves alignment of the optical system once the bracket 120 is mounted. Additionally, minor adjustments to components of the optical system may be needed to optimize the optical system. The bracket 120 may alternatively include an adjustable mount for at least one of the light sources 101 and 102. The adjustable mount 121 is preferably adjustable along two axis and functions to allow the second light source 102, and/or any additional light sources, to be aligned with the first light source 101. The adjustable mount 121 preferably has a resolution of adjustment that enables alignment of the second light source, such that at least some minimum amount of light is positioned for the focusing element 110. For example, the adjustment mount may allow for at least 90% of the collimated light to be acceptably focused onto the interrogation zone 119. The resolution is preferably achieved through and/or takes into account component manufacturing tolerances, mechanism design, system dimension variance and/or system specification (e.g. allowable vibration tolerances and temperature tolerances). The optical system 100 may, however, omit the bracket 120 and use other techniques to align the elements of the system.

In another version, the optical system 100 includes a vertical lens 122 that functions to align the multichromatic collimated beam with the interrogation zone of the flow cytometer. The vertical lens 122 is preferably adjustable along an axis perpendicular to the path of the multichromatic collimated beam. Additionally, the adjustment axis is preferably perpendicular to the flow channel of the flow cytometer. The vertical lens 122 is preferably adjusted by turning a setscrew or alternatively any suitable mechanism may be used. The vertical lens 122 preferably has a resolution of adjustment that enables the multichromatic collimated beam to be aligned along one axis, such that at least some minimum amount of light is positioned for the focusing element 110. For example, the adjustment resolution may ensure that at least 90% of the collimated light can be acceptably focused onto the interrogation zone 119. The resolution of the vertical lens adjustment is preferably achieved through and/or takes into account component manufacturing tolerances, mechanism design, system dimension variance and/or system specification (e.g. allowable shock tolerances and temperature tolerances) The vertical lens 122 may additionally be designed to work in cooperation with the adjustable mount 121. In this additional alternative, the adjustable mount 121 and vertical lens 122 preferably adjust the multichromatic collimated beam to focus at least some minimum amount into the interrogation zone 119. The optical system 100 may, however omit the vertical lens 122 or may include any other suitable device to provide a similar functionality.

In yet another version, the optical system 100 includes a base that functions to support and align the elements of the system. In one variation, the light sources 101 and 102, the beam combining element 107 (or the bracket 120), and the flow cell 130 are all individually mounted to the base. In another variation, the light sources 101 and 102, the beam combining element 107 (or the bracket 120), and the focusing element 100 are all individually mounted to the base. The base is preferably made of a rigid material, such as steel, but may alternatively be made of any suitable material that provides support and alignment to the elements of the system.

In yet another version, the optical system 100 includes a beam shaping element 124 that functions to modify one or more characteristics of the combined collimated beam. The beam shaping element 124 preferably redistributes the irradiance and/or the phase of the combined collimated beam before the focusing element 110 focuses the combined collimated beam, but may additionally and/or alternatively manipulate any suitable characteristic of the combined collimated beam. The beam shaping element 124 is preferably located between the beam combining element 107 of the lattermost optical stage and the focusing element 124 (e.g., between the beam combining element 107 and the focusing element 124 as shown in FIG. 1, or between a second beam combining element 107' and the focusing element 124 as shown in FIG. 4).

As a person skilled in the art will recognize from the previous detailed description and from the figures and claims, modifications and changes can be made to the preferred embodiments of the invention without departing from the scope of this invention defined in the following claims.

I claim:

1. An optical system for a flow cytometer with an interrogation zone, the system comprising:
    a first optical stage including:
        a first light source that creates a first beam of a first wavelength;
        a first collimating element that collimates the first beam from the first light source;
        a second light source that creates a second beam of a second wavelength, which is different than the first wavelength;
        a second collimating element that collimates the second beam from the second light source;
        a first beam combining element that combines the collimated beams of the first and second collimating elements to form a combined collimated beam that is multichromatic; and
    a second optical stage including:
        a third light source that creates a third beam of a third wavelength, which is different than the first and second wavelengths;
        a third collimating element that collimates the third beam from the third light source; and
        a second beam combining element that combines the collimated beam of the third collimating element and the combined collimated beam to form an augmented combined beam;
    a bracket including an adjustable mount for the first light source and at least one of the second and third light sources, wherein the bracket allows for alignment of at least one of the second and third light sources relative to the first light source, and wherein the adjustable mount is adjustable along two axes; and
    a focusing element that focuses the augmented combined beam to a single point.

2. The optical system of claim 1, wherein the first light source is a blue laser and the second light source is a violet laser or a red laser.

3. The optical system of claim 2, wherein at least one of the light sources is produced by a laser diode.

4. The optical system of claim 1, wherein the focusing element is located on a flow cell of the flow cytometer.

5. The optical system of claim 4, wherein the augmented combined beam is a collimated beam, and wherein the focusing element is configured to focus light from the augmented combined beam to a single point within the flow cell.

6. The optical system of claim 5, wherein at least one of the first and second beam combining elements is a beam splitter.

7. The optical system of claim 5, wherein the focusing element is configured to focuses a portion of a collimated beam on the single point when the collimated beam is misaligned with the focusing element.

8. The optical system of claim 7, further including an adjustable vertical lens positioned between the second beam combining element and the flow cell, wherein the adjustable vertical lens modifies a position of the augmented combined beam.

9. The optical system of claim 7, further including a changeable optical filter configured to absorb spurious emissions.

10. The optical system of claim 4, further including a beam shaping element that redistributes the phase of the augmented combined beam before the focusing element focuses the augmented combined beam.

11. The optical system of claim 1, further comprising a flow cell that defines the interrogation zone for the flow cytometer, wherein the focusing element is located on the flow cell.

12. The optical system of claim 11, wherein the augmented combined beam is a collimated beam, and wherein the focusing element is configured to focus light from the augmented combined beam to a single point within the flow cell.

13. The optical system of claim 12 wherein the focusing element is configured to focus a portion of a collimated beam on the single point when the collimated beam is misaligned with the focusing element.

14. The optical system of claim 13, further including an adjustable vertical lens positioned between the second beam combining element and the flow cell, wherein the adjustable vertical lens modifies a position of the augmented combined beam.

15. The optical system of claim 13, further including a changeable optical filter configured to absorb spurious emissions.

16. The optical system of claim 11, further including a beam shaping element that redistributes the phase of the augmented combined beam before the focusing element focuses the augmented combined beam.

17. The optical system of claim 1 wherein the first collimating element is mounted to the first light source, and wherein the second collimating element is mounted to the second light source.

18. The optical system of claim 1 further comprising a flow cell that defines the interrogation zone for the flow cytometer, wherein the focusing element is located on the flow cell.

* * * * *